US008246682B2

(12) United States Patent
Slivka et al.

(10) Patent No.: US 8,246,682 B2
(45) Date of Patent: Aug. 21, 2012

(54) METHODS AND DEVICES FOR EXPANDING A SPINAL CANAL USING BALLOONS

(75) Inventors: Michael Andrew Slivka, Taunton, MA (US); Michael Jacene, Blackstone, MA (US); Michael J O'Neil, West Barnstable, MA (US); Anita Barnick, Berkley, MA (US); Alfred J. Fichera, Raynham, MA (US); John C. Voellmicke, Franklin, MA (US)

(73) Assignee: DePuy Spine, Inc., Raynham, MA (US)

( * ) Notice: Subject to any disclaimer, the term of this patent is extended or adjusted under 35 U.S.C. 154(b) by 599 days.

(21) Appl. No.: 12/336,035

(22) Filed: Dec. 16, 2008

(65) Prior Publication Data

US 2010/0152854 A1    Jun. 17, 2010

(51) Int. Cl.
*A61F 2/44* (2006.01)
(52) U.S. Cl. .................. 623/17.11; 606/246; 606/279
(58) Field of Classification Search .... 623/17.11–17.16; 606/60, 246, 279
See application file for complete search history.

(56) References Cited

U.S. PATENT DOCUMENTS

| | | | |
|---|---|---|---|
| 5,480,442 A | 1/1996 | Bertagnoli | |
| 5,571,189 A | 11/1996 | Kuslich | |
| 6,049,026 A | 4/2000 | Muschler | |
| 6,080,157 A | 6/2000 | Cathro | |
| 6,358,254 B1 | 3/2002 | Anderson | |
| 6,660,007 B2 * | 12/2003 | Khanna | 606/284 |
| 6,723,095 B2 | 4/2004 | Hammerslag | |
| 6,899,713 B2 | 5/2005 | Shaolian | |
| 6,997,953 B2 * | 2/2006 | Chung et al. | 623/17.11 |
| 7,744,630 B2 * | 6/2010 | Lancial | 606/247 |
| 2002/0068975 A1 | 6/2002 | Teitelbaum | |
| 2002/0082598 A1 | 6/2002 | Teitelbaum | |
| 2002/0082600 A1 | 6/2002 | Shaolian | |
| 2002/0198526 A1 | 12/2002 | Shaolian | |
| 2003/0045885 A1 | 3/2003 | Margulies | |
| 2003/0125740 A1 | 7/2003 | Khanna | |
| 2004/0006341 A1 | 1/2004 | Shaolian | |
| 2004/0006344 A1 | 1/2004 | Nguyen | |
| 2004/0030388 A1 * | 2/2004 | Null et al. | 623/17.11 |
| 2005/0107877 A1 * | 5/2005 | Blain | 623/16.11 |
| 2006/0004358 A1 | 1/2006 | Serhan | |
| 2007/0055373 A1 * | 3/2007 | Hudgins et al. | 623/17.11 |
| 2007/0213719 A1 | 9/2007 | Hudgins | |
| 2008/0009865 A1 * | 1/2008 | Taylor | 606/61 |
| 2010/0069960 A1 * | 3/2010 | Chaput | 606/249 |
| 2010/0161056 A1 * | 6/2010 | Voellmicke et al. | 623/17.11 |
| 2010/0185240 A1 * | 7/2010 | Mangione et al. | 606/250 |
| 2010/0241165 A1 * | 9/2010 | Konieczynski et al. | 606/248 |
| 2010/0241230 A1 * | 9/2010 | Mazzuca et al. | 623/17.11 |
| 2011/0106083 A1 * | 5/2011 | Voellmicke et al. | 606/70 |

FOREIGN PATENT DOCUMENTS

| | | |
|---|---|---|
| WO | WO 0245765 | 6/2002 |
| WO | WO 03020110 | 3/2003 |

OTHER PUBLICATIONS

PCT Search Report mailed Mar. 20, 2012 for PCT/US09/67830.

* cited by examiner

*Primary Examiner* — Ellen C Hammond

(57) ABSTRACT

An in-situ formed laminoplasty implant comprising an expandable bag containing a flowable, hardenable composition, wherein the implant may be shaped to act as a laminoplasty strut and be rigidly connected to a prepared lamina space.

9 Claims, 9 Drawing Sheets

101

METHODS AND DEVICES FOR EXPANDING A SPINAL CANAL USING BALLOONS

BACKGROUND OF THE INVENTION

Spinal stenosis is the narrowing of the spinal cord canal, and can result in pain, weakness in arms and/or legs, and unsteadiness in the gait. For mild conditions, conservative treatment may be sufficient. When symptoms are severe or progressive, however, cervical laminoplasty surgery may be required to enlarge the spinal canal to relieve compression of the spinal cord. Common indications which give rise to a need for laminoplasty surgery include stenosis of the spinal canal, ossification of the posterior longitudinal ligament (OPLL), and spondylotic myelopathy.

Surgical techniques used to perform laminoplasty surgery can vary and will depend on many factors, including the source of the spinal cord compression, the number of vertebral segments involved in the disease process, and the cervical alignment. Two common surgical laminoplasty techniques include open door laminoplasty and midline splitting, or "French Door", laminoplasty. In open door laminoplasty, the lamina is cut on one side and hinged on the other side. The lamina is then rotated to open the canal, and sutures are placed on the hinged side to maintain the opening, or a bone graft and/or plate is placed in the opening. Eventually, bone growth will fuse the hinge maintaining the open position. In French Door laminoplasty, both sides of the lamina are hinged, and the spinous process is bisected. Both halves are then rotated outwards, and a bone graft is placed between the halves to secure the opening.

Several devices exists for maintaining or stabilizing the lamina in the open or split position. U.S. Pat. No. 6,080,157 (Cathro), for example, discloses a device for stabilizing the lamina after open door laminoplasty surgery. The device includes a spacer which is shaped to engage between severed edges of a lamina, and a retainer attached to the spacer which is adapted to maintain the spacer in an operative position. U.S. Pat. No. 6,358,254 (Anderson) also discloses a device for expanding the spinal canal. The device includes two stents, two washers, two fasteners, and a cable. In use, pedicle cuts are made in the vertebra, and a fastener is then inserted into each cut, through a washer and a stent, to expand the cut bone. The cable is then attached to each washer and strapped around the posterior portion of the vertebrae to stabilize the expanded canal and allow the vertebrae to heal with the spinal canal expanded.

While these devices have proven effective, they can be difficult to implant, resulting in increased medical costs. Moreover, the devices do not have a substantially low-profile, and thus can potentially cause damage to surrounding tissue and/or to the spinal cord. The devices are also not designed to restore the natural dynamics of the cervical spine, and thus can cause discomfort to the patient.

Accordingly, there exists a need for an improved laminoplasty implant that is effective to maintain and stabilize the position of the lamina after laminoplasty surgery. Moreover, there is a need for a device that can be easily and safely implanted, that will allow for permanent bony incorporation when used with bone growth promoting materials, that will allow for muscle re-attachment, and that will restore the natural dynamics of the cervical spine.

US Published Patent Application U.S. 2002/0068975 ("Shaolian") discloses formed in place orthopedic fixation devices comprising inflatable members inflated with hardenable media. Shaolian does not disclose hardenable media that is resorbable, osteoconductive, or osteoinductive. See also US Patent Publications 2002/0082598, US 2002/0082600, US2002/0198526, US 2004/0006341, US 2004/0006344 and U.S. Pat. No. 6,899,713, and PCT Patent Publication WO2003/020110.

U.S. Pat. No. 5,571,189 ("Kuslich") discloses a flexible fabric bag packed with a biological fill composition that allows bone ingrowth through the bag. Kuslich further discloses a sausage-shaped container prefilled with fill composition and positioned against the bone of adjacent vertebrae. The containers become very rigid over time and attach via bone ingrowth to the vertebrae, ultimately to provide a fusion. In particular, in FIGS. 11 and 12 of Kuslich, a bag is depicted as a sausage-shaped container which is not implanted into a disc cavity. Rather, one or more of the bag containers, prefilled with fill composition are positioned against the bone of adjacent vertebrae. The bone may be toughened to a bleeding surface to hasten bone growth into the containers. According to Kuslich, as time goes by, the containers will become very rigid and will be attached via bone ingrowth to both vertebrae where they contact native bone to provide a safe, simple fusion. The bags provide containment of the bone-growth composition to ensure that the fusion takes place where indicated. Kuslich does not disclose a filled bag that is fixed to the adjacent vertebrae at the time of implantation. Accordingly, this device is subject to undesired movement prior to fusion.

PCT Patent Publication W00245765 ("Sybert") disclosed an osteogenic band affixed to two or more vertebrae on the posterior side of the spine. Sybert does not disclose an in-situ hardenable composition.

U.S. Pat. No. 6,723,095 (Hammerslag) discloses methods of spinal fixation involving the application of a liquid medium which cures, hardens, polymerizes or otherwise serves to bind adjacent vertebrae together. Hammerslag discloses a preferred embodiment in which the liquid medium is a low viscosity cyanoacrylate-based adhesive, a composition that does not promote fusion. Although Hammerslag further teaches that "use of a medium to fix the articulate processes may be combined with methods which involve stimulating the growth of a bony mass or fusion body to fix the spine." (7, 24-27), Hammerslag does not disclose fusion of the posterolateral aspects of adjacent vertebrae.

US Patent Publication US2006-0004358 (Serhan) discloses in-situ formed spinal implant comprising a hardenable, resorbable, bone fusion-promoting composition, wherein the implant may be rigidly connected to adjacent vertebrae until fusion occurs.

SUMMARY OF THE INVENTION

The invention comprises an in-situ formed laminoplasty implant comprising an expandable bag containing a flowable, hardenable composition, wherein the implant may be shaped to act as a laminoplasty strut and be rigidly connected to a prepared lamina space.

In general, the present invention comprises methods and devices for expanding the spinal canal using expandable implants such as bags or balloons. In one preferred embodiment of the present invention, there is provided a balloon device comprising i) a pair of ends having throughholes for placing fixation elements (such as bone fasteners) therethrough, and a central intermediate portion (or belly) that, when expanded, can act as a spacer for a prepared lamina space, and iii) an inlet port for filling the cavity with a flowable, hardenable material.

In one preferred method embodiment of the present invention, there is provided a method comprising the steps of attaching one end of the balloon to the lamina portion of a vertebra using a bone fastener, cutting the lamina near the bone fastener attachment to form a lamina space having opposed end portions and opposed end faces; attaching the other end of the balloon to the bone face opposite the cut, filling the balloon cavity with a flowable hardenable material, and then allowing or causing to harden the flowable hardenable material.

In one preferred embodiment, there is provided a balloon or bladder device with a central belly acting as a spacer between bony elements and end portions comprising holes for attaching the balloon or bladder to a vertebra. In some embodiments, a spacer is not necessary, as the hinge will fuse and hold open the lamina long term.

In one preferred embodiment, there is provided a method of using a balloon or bladder to enlarge and hold open a spinal canal.

In some embodiments, there is provided an in-situ formable composition comprising a structural, osteoconductive, and resorbable component in addition to an osteoinductive component. The in-situ formable composition is delivered to the cut lamina of the spine preferably during a minimally invasive surgical procedure, and may be guided and/or contained within the area of interest using any number of bag, balloon or fabric technologies known in the art. In addition, the in-situ formable composition and/or guiding member may be anchored to the bony structures of the spine using anchors such as bone fasteners (such as bone screws), staples and suture anchors.

The hardenable aspect of the in-situ formed composition allows the composition to be flowed into place, thereby allowing for minimally invasive procedures. The structural aspect of the in-situ formed composition provides for a degree of rigidity desirable for fusion. The osteoconductive aspect of the in-situ formed composition provides an avenue for osteoprogenitor cells to enter the device. The resorbable aspect of the in-situ formed composition allows the composition to slowly degrade over time, thereby avoiding the permanence of metallic implants. The osteoinductive component of the in-situ formed composition enhances local bone growth and thus the desired fusion.

In contrast to conventional devices, this invention provides a minimally invasive means of simultaneous expansion of the spinal canal and the osteogenic capacity to fuse the adjacent vertebrae, ultimately with the patient's own bone.

Therefore, in accordance with the present invention, there is provided a method of expanding a spinal canal of a patient having a vertebra having a lamina having first and second end portions, comprising the steps of:
  a) providing an expandable laminoplasty implant comprising i) a first end portion adapted for securement to a first end portion of the lamina, ii) a second end portion adapted for securement to a second end portion of the lamina, iii) an intermediate portion between the first and second end portions, the intermediate portion having an enclosed cavity, and iv) at least one inlet port in fluid connection with the enclosed cavity;
  b) securing at least a portion of the implant to the lamina;
  c) passing a flowable, hardenable composition through the at least one inlet port and into the cavity of the implant.

DETAILED DESCRIPTION OF THE INVENTION

Figure 1:
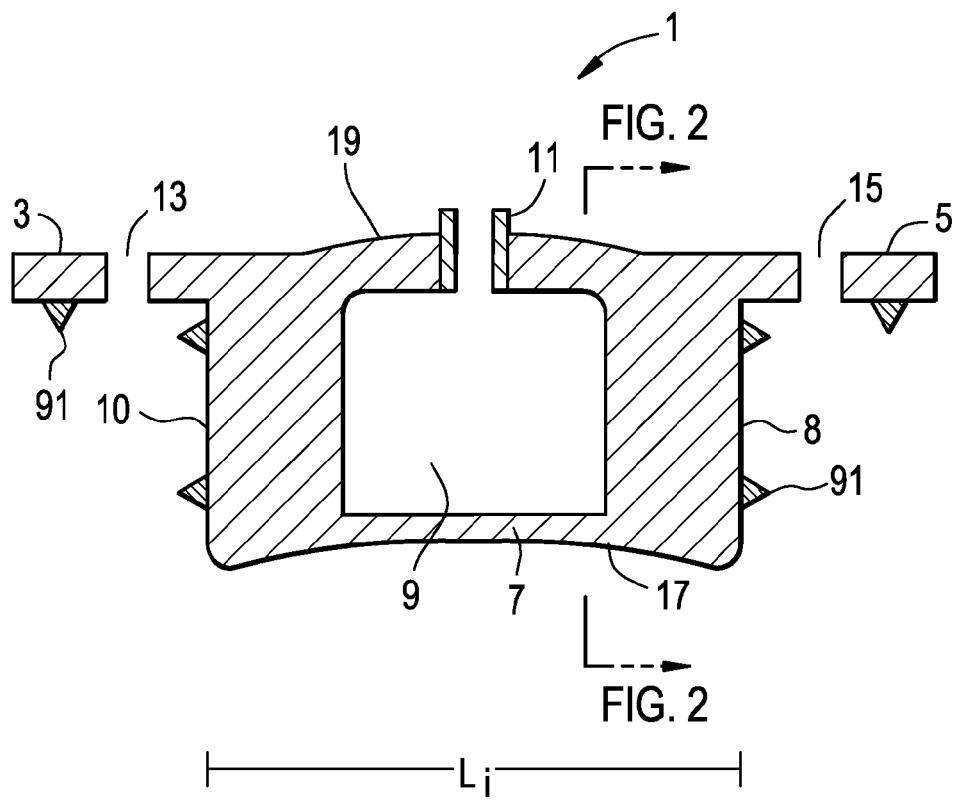
FIG. 1 is a longitudinal cross-section of the implant of the present invention.

Now referring to FIG. 1, there is provided an expandable laminoplasty implant 1 for insertion into a prepared lamina having opposing end portions and opposing faces defining a lamina space, the implant comprising:
  i) a first end portion 3 adapted for securement to a first end portion of a prepared lamina,
  ii) a second end portion 5 adapted for securement to a second end portion of a prepared lamina,
  iii) an intermediate portion 7 between the first and second end portions, the intermediate portion having an enclosed cavity 9, and
  iv) an inlet port 11 in fluid connection with the enclosed cavity.

Also in FIG. 1, the first end portion comprises a first throughhole 13 adapted for reception of a first bone fastener (not shown), while the second end portion comprises a second throughhole 15 adapted for reception of a second bone fastener (not shown). Further, the intermediate portion further comprises a concave side 17 and an opposed convex side 19. The curved nature of these sides 17, 19 mimics the natural curvature of the lamina portion the implant replaces. Lastly, the intermediate portion may also comprise first 8 and second 10 endfaces. In some preferred embodiments, when the flowable composition passes into the cavity, the first endface 8 of the intermediate portion contacts the first opposed face of the prepared lamina (1F of FIG. 5) and the second endface 10 of the intermediate portion contacts the second opposed face (1F of FIG. 5).

Figure 2:
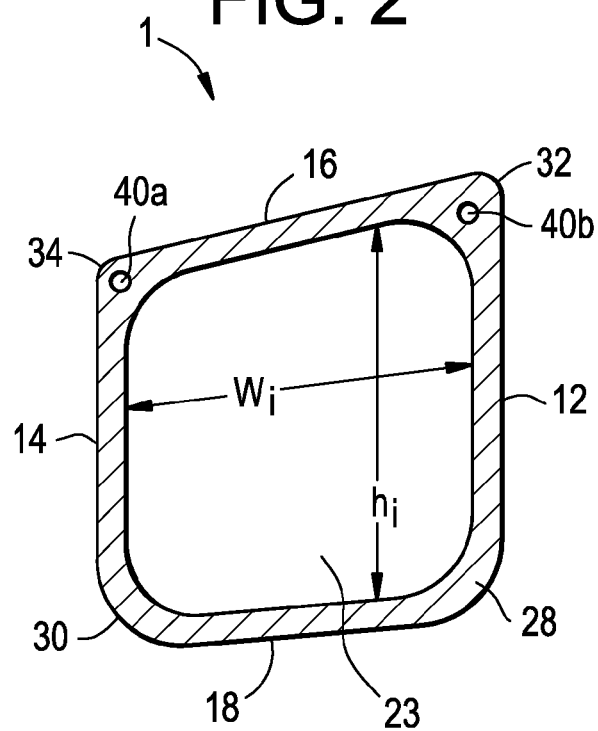
FIG. 2 is a transverse cross-section of the implant of the present invention.

The dimensions of the implant 1 can also vary depending on the intended use. Now referring to FIGS. 1 and 2, preferably, the intermediate portion 7 of the implant 1 has a length $L_i$ (FIG. 1), width $w_i$ (FIG. 2), and height $h_i$ (FIG. 2) that is sufficient to fit within a bisected lamina and to provide the necessary expansion of the spinal canal. More preferably, the intermediate portion of implant 1 has a length $L_i$ extending between the first and second opposing endfaces 8,10 that is in the range of about 4 mm to 25 mm, a height $h_i$ extending between the posterior and anterior side's 16, 18 that is in the range of about 2 mm to 10 mm, and a width $w_i$ extending between the caudal and cephalad sides 12, 14 that is in the range of about 5 mm to 15 mm. A person having ordinary skill in the art will appreciate that the dimensions of the implant can vary depending on the intended use.

Figure 6:
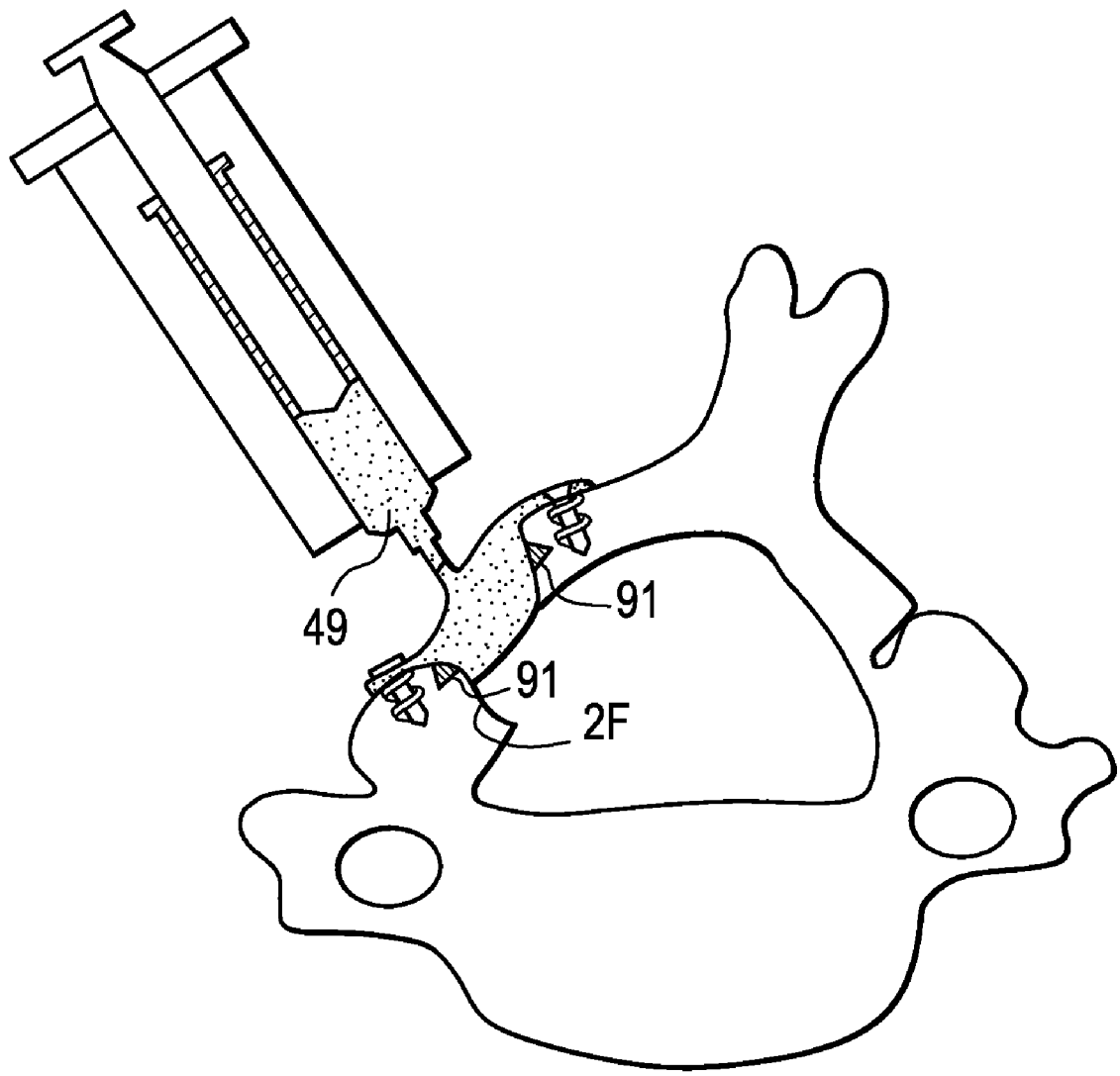
FIG. 6 discloses filling the implant of the present invention with a flowable, hardenable material, thereby causing the lamina to rotate away from the cut end, thus expanding the spinal canal and allowing the spinal cord to be decompressed.
Figure 7:
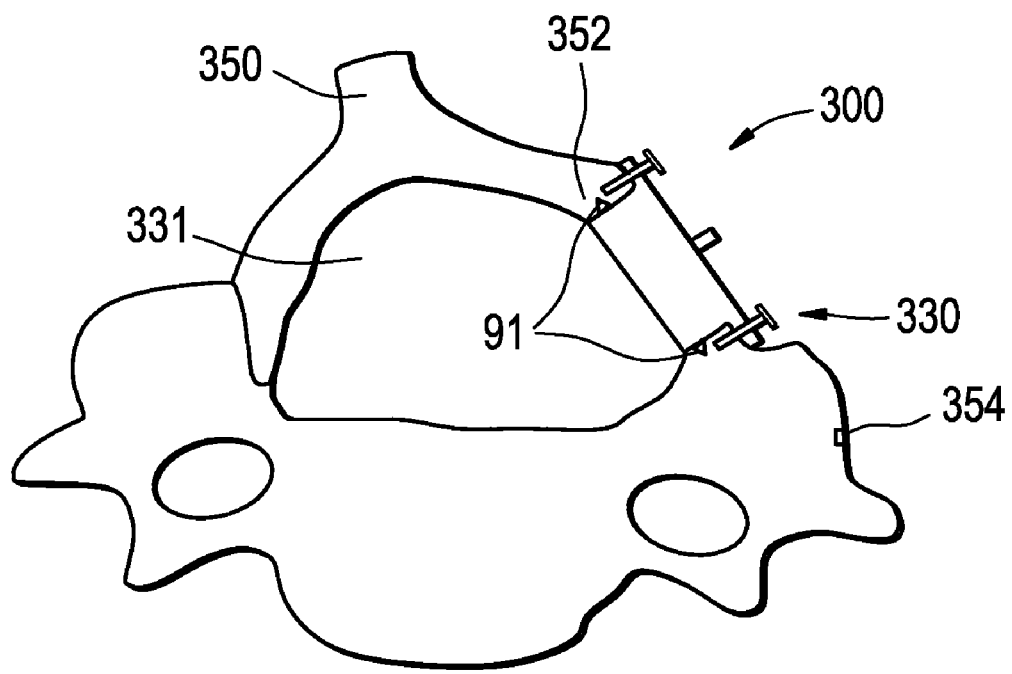
FIG. 7 is an axial view of the implant of the present invention implanted within a lamina.
Figure 8:
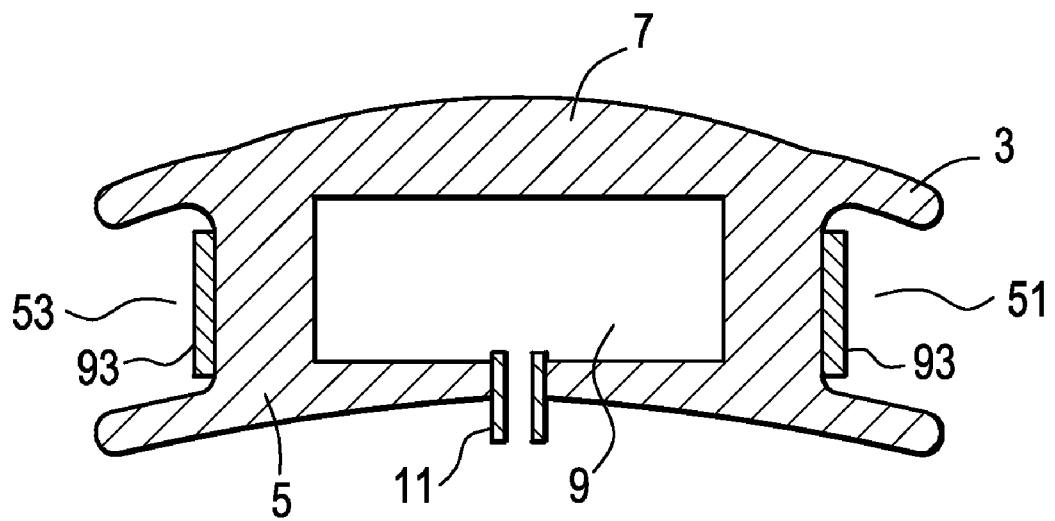
FIG. 8 is a cross-section of an implant of the present invention adapted whose concave ends are adapted to secure to the opposed end portions of the prepared lamina.

In addition, the laminoplasty device can include mechanical or biologic bony attachment features. The mechanical features enhance short term securement to the lamina while the biologic features provide long term attachment via biologic surfaces which enable bony in-growth. These features may be mechanical features 91 (as shown in FIGS. 1, 6 and 7), which may include roughened surfaces, barbs, fins, teeth, and spikes. The biologic features may be in-growth surfaces 93 (as shown in FIG. 8) which can include biologic meshes such as collagen, Ti Mesh, or PET. In some embodiments, in growth surfaces can replace the mechanical features shown in FIG. 1. In some embodiments, the attachment feature may include both mechanical and biologic attachment features in the same location.

Figure 3:
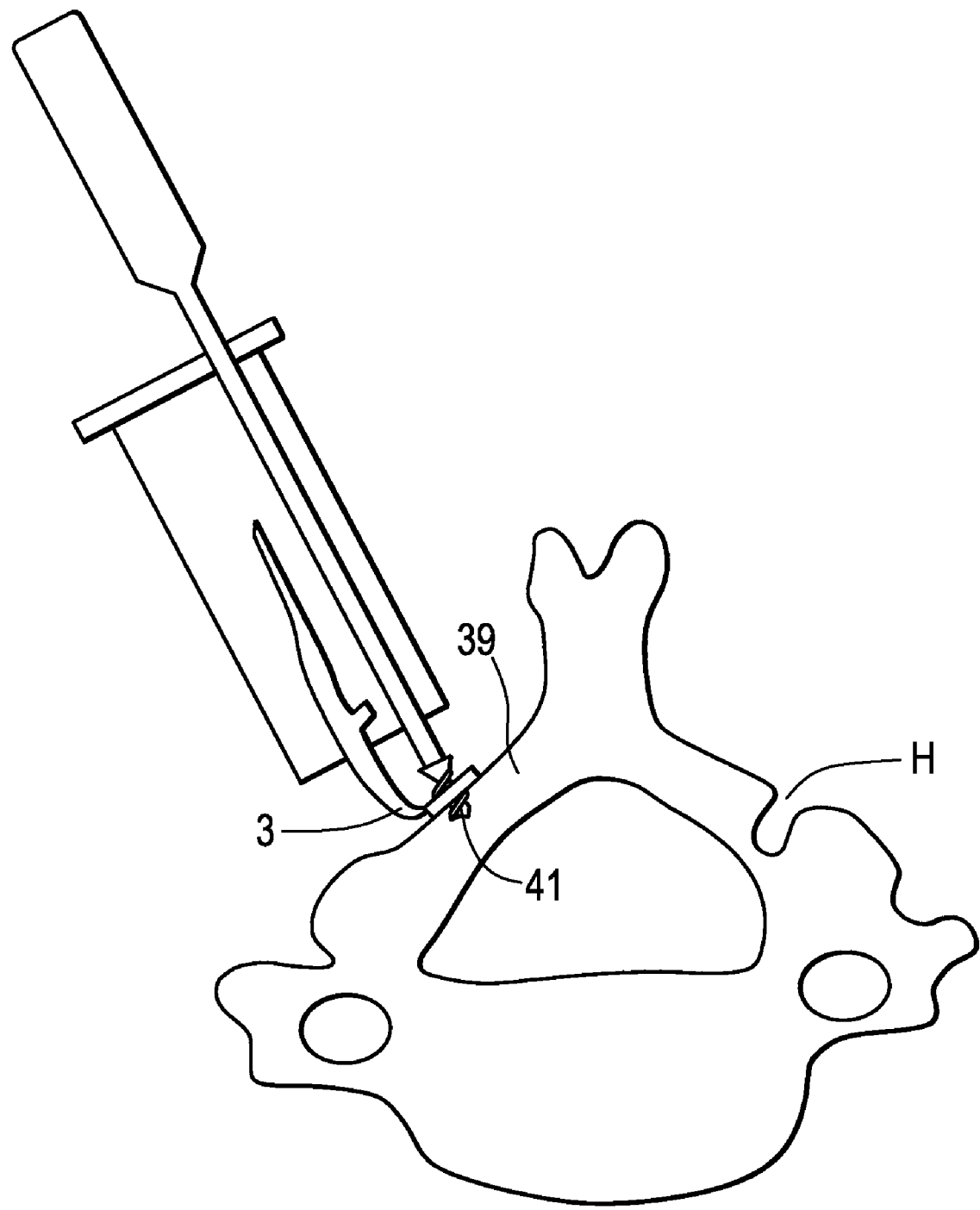
FIG. 3 discloses securing the implant of the present invention to a first end portion of a lamina.
Figure 4:
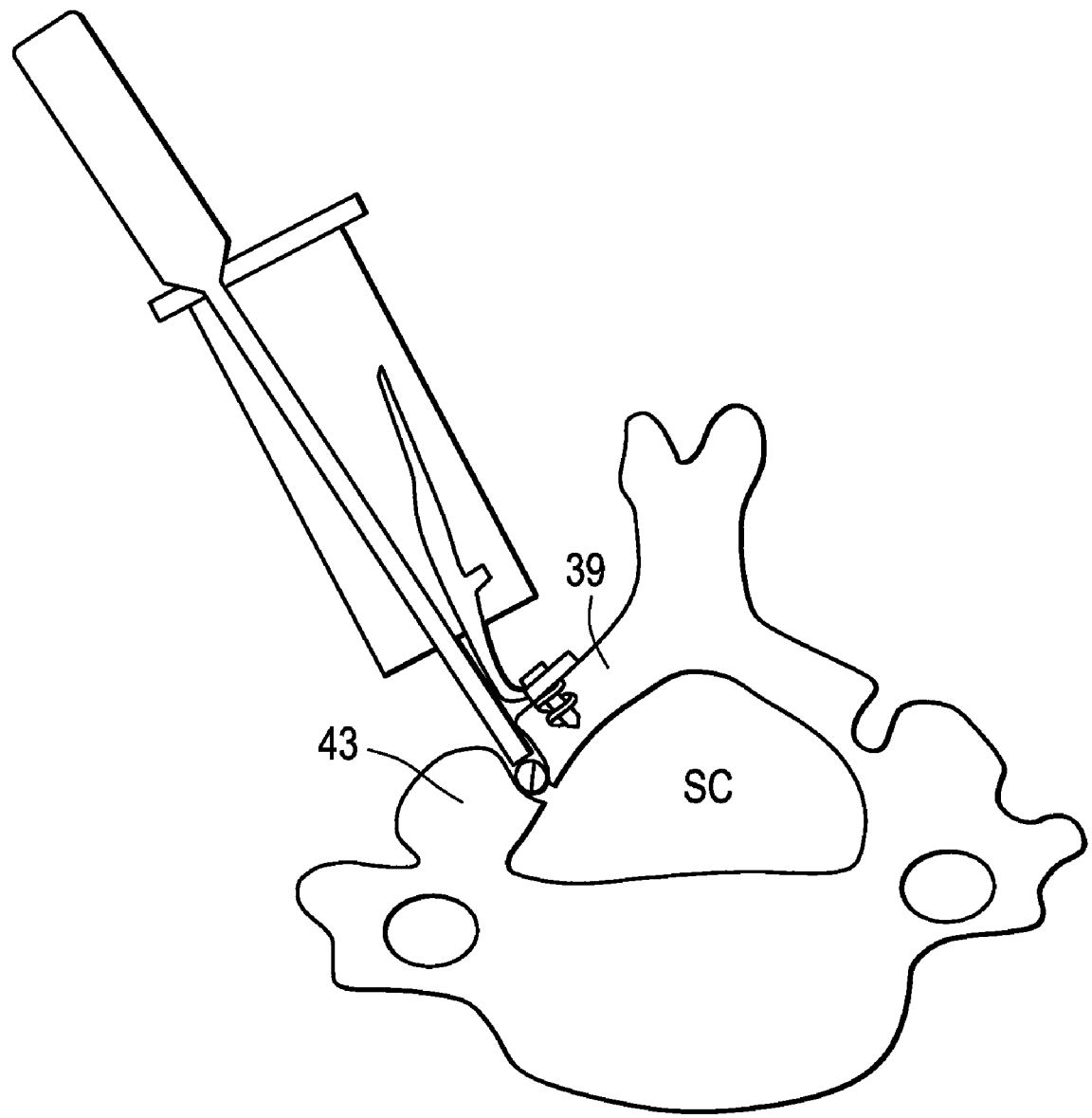
FIG. 4 discloses removing a portion of the lamina to create opposing faces defining a lamina space.
Figure 5:
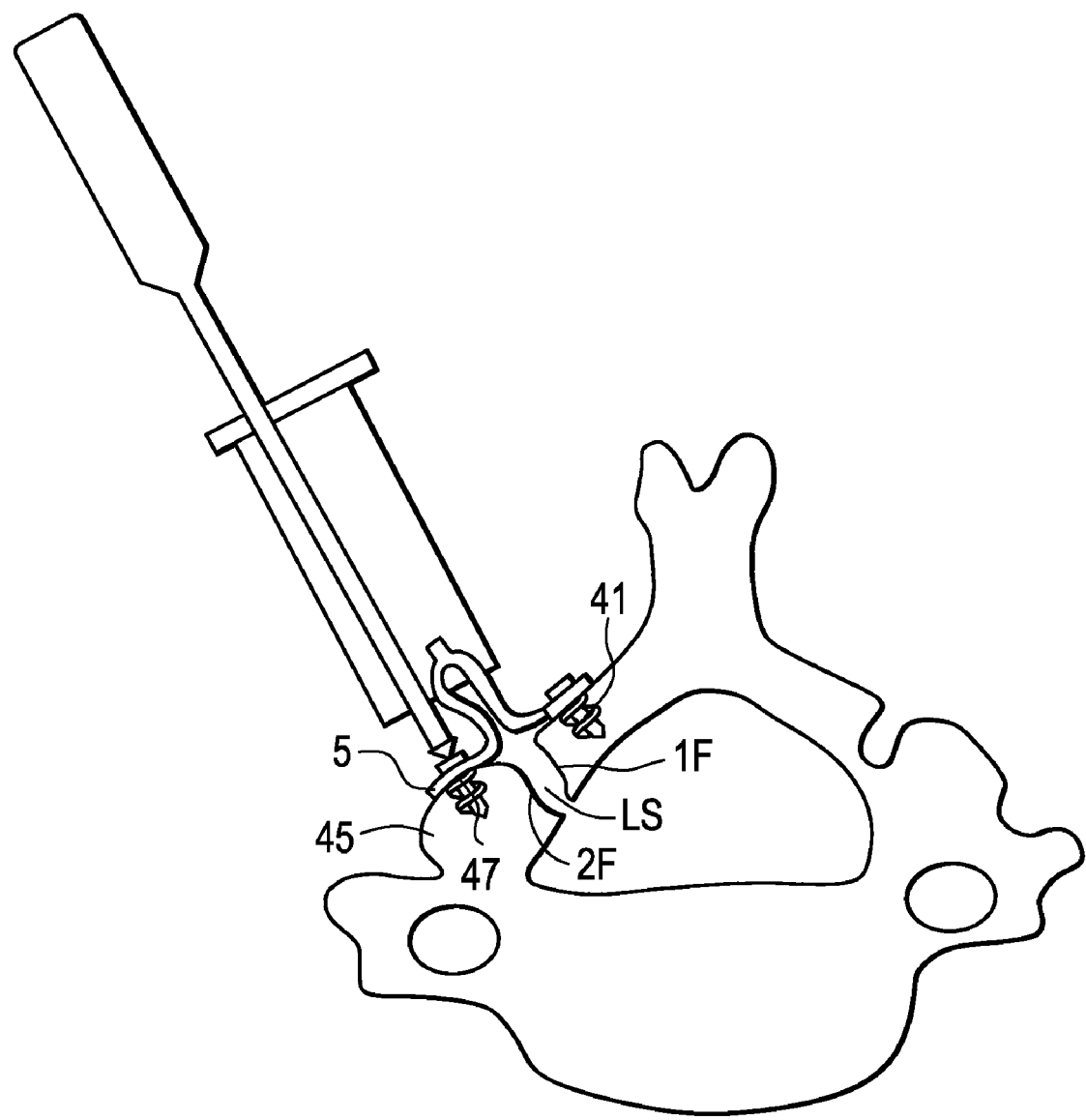
FIG. 5 discloses securing the implant of the present invention to a second end portion of the lamina.

FIGS. 3-6 illustrate a preferred method and device of this invention. In FIG. 3, a minimally invasive surgical (MIS) approach is used to perform a cervical spine decompression procedure following a conventional open-door laminoplasty technique. The hinge H in the opposing side of the lamina has already been prepared. A first end portion 3 of the balloon device is being fixed to a first end portion 39 of the lamina using a first bone fastener 41 through a throughhole of approximately 15 mm diameter. In FIG. 4, a burring device is being used to essentially bisect the lamina between its first end 39 and second end 43. The cut travels all the way through to the spinal canal SC to create a prepared lamina having a first opposed face 1F, a second opposed face 2F and a lamina space LS, while pushing the balloon device to the side of the port. Inserting the first fastener 41 into the first end 39 of the lamina prior to cutting the lamina provides great advantage in ease and speed of implantation because the lamina can become undesirably mobile once the first side is cut and a hinge made in the second side. In FIG. 5, the unattached second end portion 5 of the balloon device is fixed to the second end portion 45 of the lamina using a second bone fastener 47. In FIG. 6, the balloon device is being filled with a flowable hardenable material 49, which causes the lamina to rotate away from the second opposing face 2F of the prepared lamina, thus expanding the spinal canal and allowing the spinal cord to be decompressed. The hardeneable material may harden through a typical thermoplastic or thermoset process, but preferably may be accelerated using light activation.

In some embodiments, the cavity can extend to the fastener holes.

Therefore, in accordance with the present invention, there is provided a method of expanding a spinal canal of a patient having a vertebra having a lamina having first and second end portions, comprising the steps of:
a) providing an expandable laminoplasty implant comprising i) a first end portion having a first throughhole, a second end portion having a second throughhole, iii) an intermediate portion between the first and second end portions, the intermediate portion having an enclosed cavity, and iv) an inlet port in fluid connection with the enclosed cavity;
b) securing the first end portion of the implant to the first end portion of the lamina;
c) removing a segment of the lamina to form a prepared lamina having opposing faces defining a lamina space;
d) securing the second end portion of the implant to the second end portion of the lamina;
e) inserting the implant into the lamina space
f) passing a flowable, hardenable composition through the inlet port and into the cavity of the implant, and
g) hardening the flowable, hardenable composition.

In one embodiment, the lamina is distracted using an auxiliary tool (not shown) prior to inflating the balloon, thus minimizing the stresses on the balloon prior to inflation.

In one embodiment, the balloon comprises a porous surface (such as a fabric) for encouraging reattachment of the muscle, ligaments and bone that were removed in order to perform the procedure.

In one embodiment, the balloon inlet port comprises a valve, such as a one way valve or a two-way valve. More preferably, the valve is an inverse tube valve that leaves no tail and requires no significant added volume as it is collapsed during insertion and contained following expansion.

Similar devices and procedures may be used for bilateral en-bloc laminoplasty or midline "French door" laminoplasty.

In order to facilitate placement of an implant in a split spinous process, the implant can optionally include one or more radiopaque markers disposed therein. The radiopaque markers are configured to provide an x-ray visible reference to indicate the position of the implant with respect to an anatomical structure when the implant is positioned within an interstitial space. The markers can have virtually any configuration, and can be positioned around and/or within the implant. The position of the markers should be adapted to facilitate accurate placement of the implant in the split spinous process. Referring back to FIG. 2, the implant 1 is shown having markers 40a and 40b extending along edges 32 and 34. The markers 40a, 40b are each in the form of an elongate wire, and are disposed within the body of the implant 1. Preferably, the body of the implant 1 is formed from a radiolucent material to allow the radiopaque markers to be distinguished from the implant 1 in an x-ray image. Preferably, edges 28, 30 32, and 34 are rounded.

The marker strip can also be formed from a variety of radiopaque materials including, for example, metals, polymers, filling salts, ceramics, and combinations thereof. Examples of suitable metals include titanium, stainless steel, tantalum, cobalt chromium, aluminum, and combinations thereof. A person having ordinary skill in the art will appreciate that the body can be formed from a radiopaque material, and the marker strip can be formed from a radio-lucent material. In some embodiments, a piece of radio-opaque wire can be weaved into the balloon in order to perform post-operative imaging.

FIG. 7 illustrates the implant 300 in use disposed within a vertebra 350 of a patient's spinal column. The implant 300 is positioned between a bisected lamina 354 of the vertebra 350, thereby enlarging the spinal canal 331. The fixation device, e.g., the bone fastener 330, is disposed through the throughhole in the end portion of the implant and threaded into the lamina 354 to secure the position of the implant 300 with respect to the vertebra 350.

Now referring to FIG. 8, in another embodiment, the balloon device does not have anchor points for fixation via bone fasteners or other types of anchors—it is simply placed between the cut ends of the bone and inflated with a flowable, hardenable material to enlarge the spinal canal. The ends of the balloon device are preferably configured to cradle the cut ends of the lamina bone such that it is less likely to become displaced from the site upon balloon inflation.

Therefore, there is provided an expandable laminoplasty implant comprising:
i) a first end portion 3 having a first substantially concave portion 51 adapted for securement to a first end portion of a prepared lamina, ii) a second end portion 5 having a second substantially concave portion 53 adapted for securement to a second end portion of a prepared lamina, iii) an intermediate portion 7 between the first and second end portions, the intermediate portion having an enclosed cavity 9, and iv) an inlet port 11 in fluid connection with the enclosed cavity.

In some embodiments (not shown), the enclosed cavity will have an opening (exclusive of the inlet port opening) adapted to open onto the lamina, so that a portion of the hardenable material may escape the cavity an attach to the lamina.

While not illustrated, an implant according to the present invention can include a variety of other features to facilitate placement of the implant in the split spinous process or lamina. By way of non-limiting example, the implant can include a number of bone engaging surface features formed on the end surfaces. The bone engaging surface features are preferably adapted to engage the cut portion of the split spinous process or lamina to facilitate the secure placement of the implant. In another embodiment, the implant can be adapted to mate to an insertion tool for inserting the implant into the split spinous process. For example, the implant can be used in conjunction with a distractor or spreader device. A person having ordinary skill in the art will appreciate that a variety of insertion tools can be used with the implant of the present invention, and that the implant can be modified to work with such a tool.

Figure 9A:
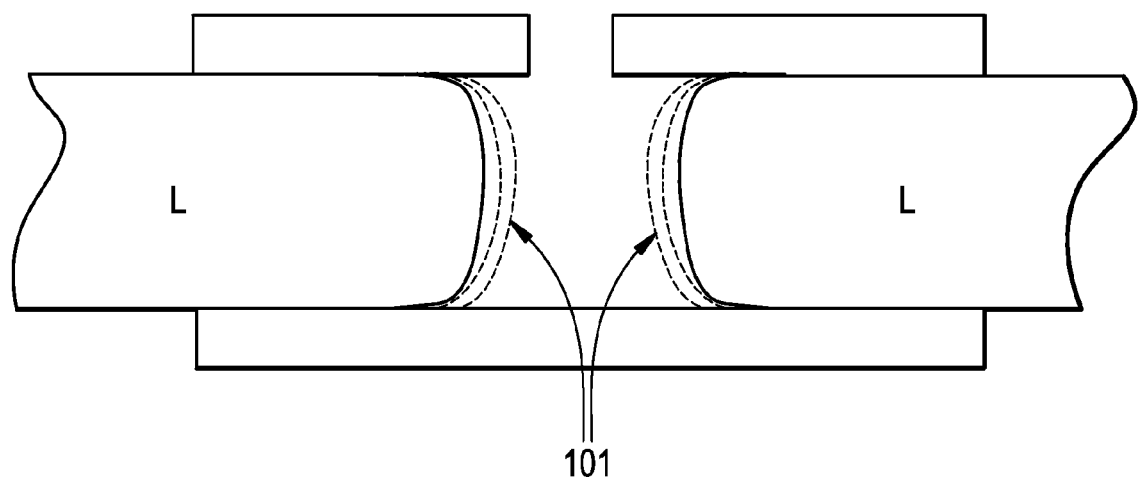
FIGS. 9a and 9b disclose cross-sections of the in-situ expandable device including permeable walls in its respective pre-inflation and post-inflation configurations.
Figure 9B:
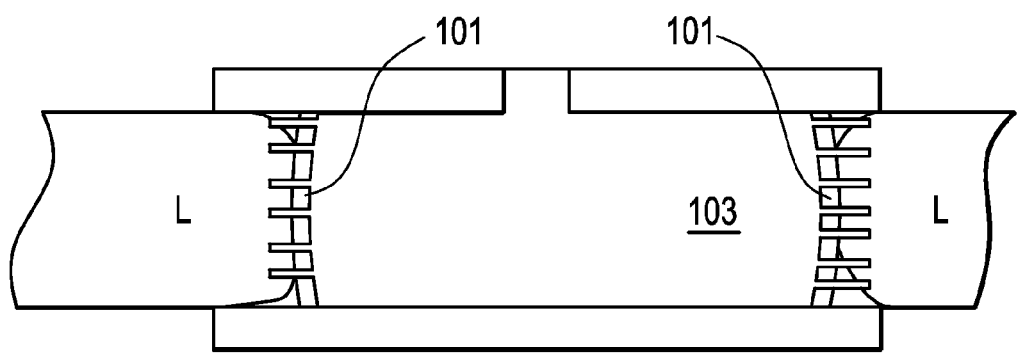

Now referring to FIGS. 9a and 9b, the expandable device could include permeable walls 101. The walls (which may be made of mesh) allow for a maximum pressure to be achieved before allowing the hardenable material 103 to permeate and interdigitate with the lamina L. The permeable wall can be made of a textile polymer mesh. FIGS. 9a and 9b disclose cross-sections of the in-situ expandable device including permeable walls in its respective pre-inflation and post-inflation configurations.

Figure 10A:
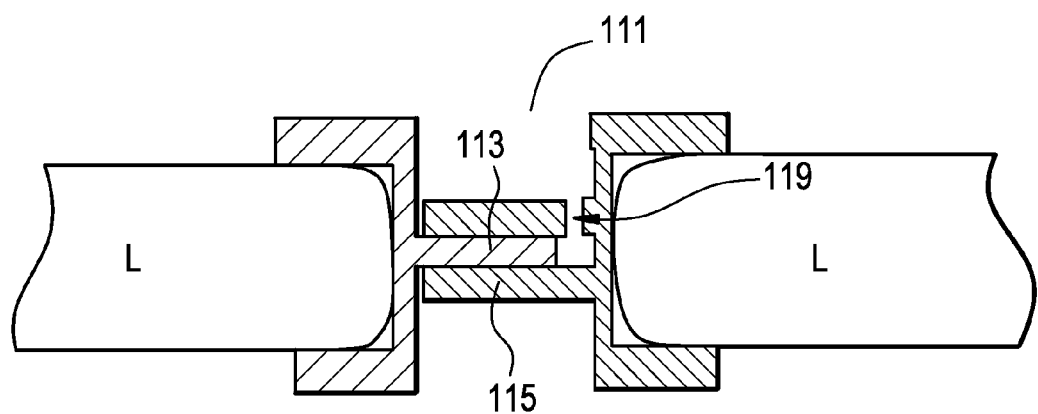
FIGS. 10a and 10b disclose cross-sections of the in-situ expandable piston device in its respective pre-expansion and post-expansion configurations.
Figure 10B:
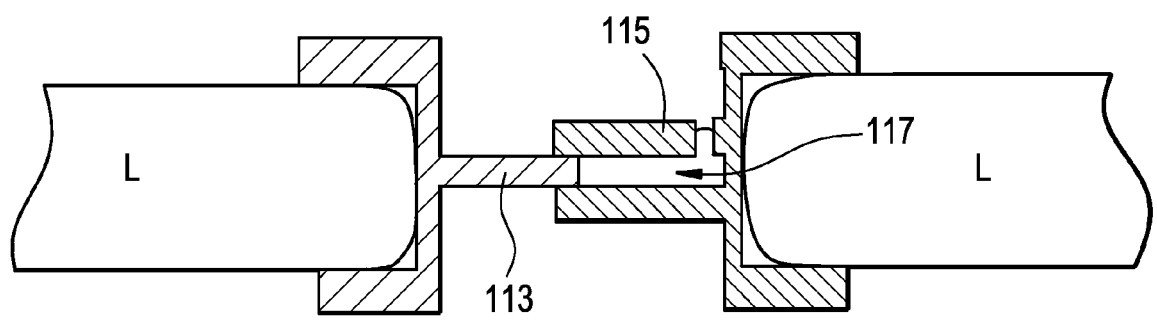

Now referring to FIGS. 10a and 10b, the intermediate portion 111 of the expandable device could be a two-piece piston design, wherein a male piece 113 is disposed within and is slidably engaged within a female piece 115 and creates a substantially closed cavity. The hardenable material 117 is injected into the cavity via an injection port 119 in the female piece, thereby forcing the cavity open and the two pieces apart, effectively distracting the lamina L. FIGS. 10a and 10b disclose cross-sections of the in-situ expandable piston device in its respective pre-expansion and post-expansion configurations.

Figure 11A:
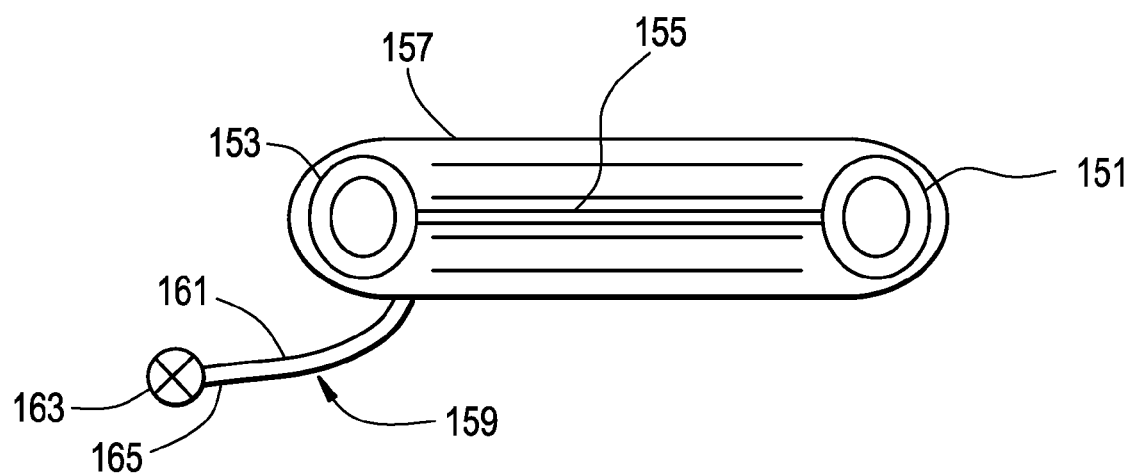
FIGS. 11a-11c disclose various views of a constrained balloon laminoplasty device of the present invention.
Figure 11B:
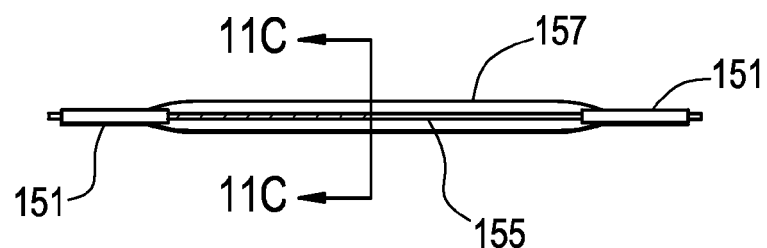
Figure 11C:
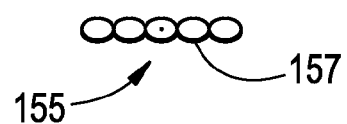

FIGS. 11a-11c disclose various views of a constrained balloon laminoplasty device of the present invention. Now referring to FIGS. 11-11c, there is provided an expandable laminoplasty implant for insertion into a prepared lamina having opposing end portions and opposing faces defining a lamina space, the implant comprising:

i) a first end portion 151 (preferably a metallic washer, grommet or eyelet) adapted for securement to a first end portion of a prepared lamina, ii) a second end portion 153 (preferably a metallic washer, grommet or eyelet) adapted for securement to a second end portion of a prepared lamina, iii) an expandable intermediate portion 157 between the first and second end portions, the intermediate portion having an enclosed cavity (not shown) into which an injectable polymer is injected, iv) an inlet port 159 in fluid connection with the enclosed cavity, and.

v) a cable 155 connecting the first and second end portions to limit extension and constrain the intermediate portion during and after expansion of the intermediate portion.

In preferred embodiments, the inlet port 159 has a fill tube 161 with a check valve 163 on its proximal end 165. The fill tube can be snapped or cut off at its base after the polymer has cured, thereby removing complexity from the implant. Preferably, the expandable intermediate portion 157 comprises a balloon comprising two sheets that are radiofrequency welded together around their matching perimeters and onto the washers. Longitudinal welds that constrain the balloon sheets to a final thickness (analogous to an inflatable pool raft) are shown in FIG. 11a as horizontal lines extending substantially from the first eyelet to the second eyelet.

Although not particularly preferred, also in accordance with the present invention, the lamina space can be prepared prior to securing the implant to the lamina. Thus, there is provided a method of expanding a spinal canal of a patient having a vertebra, comprising the steps of:

a) removing a segment of a lamina of the vertebra to form a prepared lamina having opposing end portions and opposing faces defining a lamina space;

b) providing an expandable laminoplasty implant comprising i) a first end portion having a first throughhole, a second end portion having a second throughhole, iii) an intermediate portion between the first and second end portions, the intermediate portion having an enclosed cavity, and iv) an inlet port in fluid connection with the enclosed cavity;

c) securing the first end portion of the implant to the first end portion of the prepared lamina (preferably by passing a first bone fastener through the first throughhole of the implant)

d) securing the second end portion of the implant to the second end portion of the prepared lamina (preferably by passing a second bone fastener through the second throughhole of the implant);

e) inserting the implant into the lamina space;

f) passing a flowable, hardenable osteogenic composition through the inlet port and into the cavity of the implant, g) hardening the flowable, hardenable osteogenic composition.

The materials used for form a laminoplasty cage according to the present invention can vary. Preferably, the body is formed from a rigid, semi-rigid, or flexible radio-lucent material. More preferably, the body is formed from materials such as polymers, ceramics, composite materials, and combinations thereof. Examples of suitable polymers include polyether sulfone, polycarbonate, PET, UHMWPE (including Dyneema fibers), bioabsorbable polymers, polyaryletherketones, and carbon fiber reinforced polymers. The implant can alternatively, or in addition, be formed from a variety of metals, including titanium, titanium alloys, chrome alloys, and stainless steel.

Compositions to be used in this invention are known in the art. Hardenable non-resorbable materials include polymethylmethacrylate (PMMA), cyanoacrylates, diglicidyl ether dimethacrylate, triethyleneglycol dimethacrylate; and epoxy compositions with or without filler materials. In some embodiments, the hardenable non-resorbable material can also be photopolymerizable.

Hardenable, resorbable compositions include setting ceramics, polymerizable monomers and polymers, polymers flowable at temperatures above body temperature, and polymers solubilized in a biocompatible solvent. Examples of resorbable setting ceramics include calcium phosphates, hydroxyapatites and calcium sulfates. Examples of polymerizable resorbable monomers and polymers include poly(propylene fumarate), polyoxaesters, polyurethanes and polyanhydrides. In one preferred embodiment, the hardenable composition is a photopolymerized polyanhydride. In this embodiment, irradiation can be used to control the polymerization process, therefore, a partially polymerized putty can be made, then hardened by continuing the polymerization with irradiation after the composition has been placed. Examples of resorbable polymers flowable at temperatures above body temperature include polymers and copolymers of lactic acid, glycolic acid, carbonate, dioxanone, and trimethylene carbonate. An example of a biocompatible solvent that can be used to solubilize the aforementioned polymers include dimethyl sulfoxide.

In order to improve the osteoconductivity of the aforementioned hardenable, resorbable compositions, they may be delivered to the site as an in-situ formed porous scaffold. Techniques of in situ forming porous scaffolds are known in the art and include porogen leaching and foaming with gas-producing elements.

In preferred embodiments of this invention, the hardenable, resorbable compositions incorporate an osteoinductive component. Osteoinductive components include growth factors such as bone morphogenetic proteins that can be grafted onto or mixed into said hardenable compositions. The term "growth factors" encompasses any cellular product that modulates the growth or differentiation of other cells, particularly connective tissue progenitor cells. The growth factors that may be used in accordance with the present invention include, but are not limited to, members of the fibroblast growth factor family, including acidic and basic fibroblast growth factor (FGF-1 and FGF-2) and FGF-4; members of the platelet-derived growth factor (PDGF) family, including PDGF-AB, PDGF-BB and PDGF-AA; EGFs; members of the insulin-like growth factor (IGF) family, including IGF-I and -II; the TGF-.beta. superfamily, including TGF-.beta.1, 2 and 3 (including MP-52); osteoid-inducing factor (OIF), angiogenin(s); endothelins; hepatocyte growth factor and keratinocyte growth factor; members of the bone morphogenetic proteins (BMP's) BMP-1, BMP-3; BMP-2; OP-1; BMP-2A, BMP-2B, and BMP-7, BMP-14; HBGF-1 and HBGF-2; growth differentiation factors (GDF's), members of the hedgehog family of proteins, including indian, sonic and desert hedgehog; ADMP-1; members of the interleukin (IL) family, including IL-1 thru IL-6; GDF-5 and members of the colony-stimulating factor (CSF) family, including CSF-1, G-CSF, and GM-CSF; and isoforms thereof.

In addition, bone-producing cells, such as mesenchymal stem cells (MSCs), can be delivered with the hardenable compositions by first encapsulating the cells in hydrogel spheres then mixing in. MSCs provide a special advantage because it is believed that they can more readily survive relatively harsh environments; that they have a desirable level of plasticity; and that they have the ability to proliferate and differentiate into the desired cells. In some embodiments, the mesenchymal stem cells are obtained from bone marrow, preferably autologous bone marrow. In others, the mesenchymal stem cells are obtained from adipose tissue, preferably autologous adipose tissue. In some embodiments, the mesenchymal stem cells used in an unconcentrated form. In others, they are provided in a concentrated form. When provided in concentrated form, they can be uncultured. Uncultured, concentrated MSCs can be readily obtained by centrifugation, filtration, or immuno-absorption. When filtration is selected, the methods disclosed in U.S. Pat. No. 6,049,026 ("Muschler"), the specification of which is incorporated by reference in its entirety, are preferably used. In some embodiments, the matrix used to filter and concentrate the MSCs is also administered into the container.

In another embodiment of the invention, the hardenable, resorbable, bone fusion-promoting composition is delivered to the site as a partially hardened, shapable putty. The putty can then be pressed onto the bony surfaces and around the bony structures to obtain a mechanical interlock without the use of bone anchoring elements. Alternatively, the putty can be pressed into and/or over the protruding elements of the anchors. Following shaping to the spine, the partially hardened composition will completely harden to provide a rigid fixation of the spine.

Resorbable collapsible bags include then-walled balloons, optionally perforated, fabric jackets made from the aforementioned polymers. Although the bone anchors can be made from the conventional biocompatible metals, polymers, and ceramics, they are preferable made from high strength resorbable materials, for example, sintered calcium containing ceramics such as calcium phosphate made from sintered nano-sized particulate and polymers such as poly (lactic acid) and poly (amino carbonates). In using said preferred materials, the implants will not interfere with imaging techniques such as MRI and CT.

We claim:

1. A method of expanding a spinal canal of a patient having a vertebra having a lamina having first and second end portions, comprising the steps of:
   a) providing an expandable laminoplasty implant comprising i) a first end portion having a first throughhole, ii) a second end portion having a second throughhole, iii) an intermediate portion between the first and second end portions, the intermediate portion having an enclosed cavity, and iv) an inlet port in fluid connection with the enclosed cavity;
   b) securing the first end portion of the implant to the first end portion of the lamina;
   c) removing a segment of the lamina to form a prepared lamina having opposing faces defining a lamina space;
   d) securing the second end portion of the implant to the second end portion of the lamina;
   e) passing a flowable, hardenable composition through the inlet port and into the cavity of the implant,
   f) hardening the flowable, hardenable composition,
wherein the step of securing the first end portion of the implant is performed prior to the step of removing a segment of the lamina.

2. The method of claim 1 wherein the intermediate portion comprises first and second endfaces, wherein the first endface of the intermediate portion contacts a first face of the lamina space when the composition passes into the cavity.

3. The method of claim 2 wherein the first endface of the intermediate portion pushes upon the first face of the lamina space to move the first face of the lamina away from a second face of the lamina when the composition passes into the cavity.

4. The method of claim 1 wherein the step of b) securing the first end portion of the implant to the first end portion of the prepared lamina is accomplished by passing a first bone fastener through the first throughhole of the implant.

5. The method of claim 1 wherein the step of d) securing the second end portion of the implant to the second end portion of the prepared lamina is accomplished by passing a second bone fastener through the second throughhole of the implant.

6. The method of claim 1 wherein the intermediate portion of the implant comprises a concave side and an opposed convex side.

7. The method of claim 1 wherein the flowable composition is osteogenic.

8. The method of claim 1 wherein the flowable composition is hardenable via light activation.

9. A method of expanding a spinal canal of a patient having a vertebra having a lamina having first and second end portions, comprising the steps of:
   a) providing an expandable laminoplasty implant comprising i) a first end portion adapted for securement to a first end portion of the lamina, ii) a second end portion adapted for securement to a second end portion of the lamina, iii) an intermediate portion between the first and second end portions, the intermediate portion having an enclosed cavity, and iv) an inlet port in fluid connection with the enclosed cavity;
   b) securing at least a portion of the implant to the lamina;
   c) removing a segment of the lamina to form a prepared lamina having opposing faces defining a lamina space;
   d) passing a flowable, hardenable composition through the inlet port and into the cavity of the implant,
wherein the step of securing the first end portion of the implant is performed prior to the step of removing a segment of the lamina.

* * * * *